US010485642B2

(12) United States Patent
Ogawa

(10) Patent No.: US 10,485,642 B2
(45) Date of Patent: Nov. 26, 2019

(54) OCCLUSION MEASUREMENT DEVICE AND METHOD FOR DETECTING OCCLUSAL FORCE

(71) Applicants: MOTT LLC, Tokyo (JP); GC CORPORATION, Tokyo (JP)

(72) Inventor: Mutsuo Ogawa, Tokyo (JP)

(73) Assignees: MOTT LLC, Tokyo (JP); GC CORPORATION, Tokyo (JP)

(*) Notice: Subject to any disclaimer, the term of this patent is extended or adjusted under 35 U.S.C. 154(b) by 7 days.

(21) Appl. No.: 15/112,097

(22) PCT Filed: Jan. 21, 2015

(86) PCT No.: PCT/JP2015/051568
§ 371 (c)(1),
(2) Date: Jul. 15, 2016

(87) PCT Pub. No.: WO2015/111633
PCT Pub. Date: Jul. 30, 2015

(65) Prior Publication Data
US 2016/0338812 A1    Nov. 24, 2016

(30) Foreign Application Priority Data
Jan. 21, 2014  (JP) .................................. 2014-008605

(51) Int. Cl.
*A61C 19/05*       (2006.01)
*G01L 5/00*        (2006.01)
(Continued)

(52) U.S. Cl.
CPC .............. *A61C 19/05* (2013.01); *A61C 9/008* (2013.01); *A61C 19/04* (2013.01); *G01L 1/14* (2013.01);
(Continued)

(58) Field of Classification Search
CPC ......... A61C 19/05; A61C 19/04; A61C 9/008; A61C 9/0046; G01L 1/14; G01L 1/16; G01L 5/00
(Continued)

(56) References Cited

U.S. PATENT DOCUMENTS 4,390,028 A * 6/1983 Okano ...................... G01L 1/20
433/68
4,402,326 A * 9/1983 Okano ................... A61C 19/05
348/162

(Continued)

FOREIGN PATENT DOCUMENTS

JP    S56-142430 A    11/1981
JP    S56-156137 A    12/1981
(Continued)

OTHER PUBLICATIONS

Feb. 17, 2015 International Search Report issued in Patent Application No. PCT/JP2015/051568.
(Continued)

*Primary Examiner* — Matthew M Nelson
(74) *Attorney, Agent, or Firm* — Oliff PLC

(57) ABSTRACT

An information processing device (104) performs integration processing for each intersection point for raw data outputted from an occlusal force detecting device having a sensor sheet (102) which uses an organic piezoelectric film (201), to create occlusal force data, wherein the raw data includes address information of each intersection point and data obtained based on a signal indicating a change in occlusion force.

2 Claims, 8 Drawing Sheets

(51) Int. Cl.
   *G01L 1/16* (2006.01)
   *A61C 19/04* (2006.01)
   *A61C 9/00* (2006.01)
   *G01L 1/14* (2006.01)

(52) U.S. Cl.
   CPC .................. *G01L 1/16* (2013.01); *G01L 5/00* (2013.01); *A61C 9/0046* (2013.01)

(58) Field of Classification Search
   USPC ...................................................... 433/27, 68
   See application file for complete search history.

(56) References Cited

U.S. PATENT DOCUMENTS

| | | | | |
|---|---|---|---|---|
| 4,856,993 A | * | 8/1989 | Maness | A61C 19/05 433/68 |
| 2013/0245473 A1 | * | 9/2013 | Ramanathan | A61B 5/0402 600/509 |

FOREIGN PATENT DOCUMENTS

| | | | |
|---|---|---|---|
| JP | S61-48852 | A | 3/1986 |
| JP | H03-284257 | A | 12/1991 |
| JP | H05-322679 | A | 12/1993 |
| JP | H07-20478 | A | 1/1995 |
| JP | H07-190870 | A | 7/1995 |
| JP | 2904494 | B2 | 6/1999 |
| JP | 3668312 | B2 | 7/2005 |
| JP | 2008-125872 | A | 6/2008 |
| JP | 2008-264024 | A | 11/2008 |
| JP | 2008264024 | A * | 11/2008 |
| JP | 2008264024 | A * | 11/2008 |
| JP | 4240224 | B2 | 3/2009 |
| JP | 4243843 | B2 | 3/2009 |

OTHER PUBLICATIONS

Feb. 17, 2015 Written Opinion issued in Patent Application No. PCT/JP2015/051568.

* cited by examiner

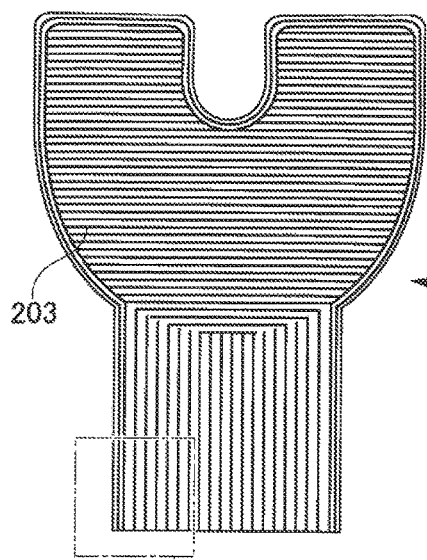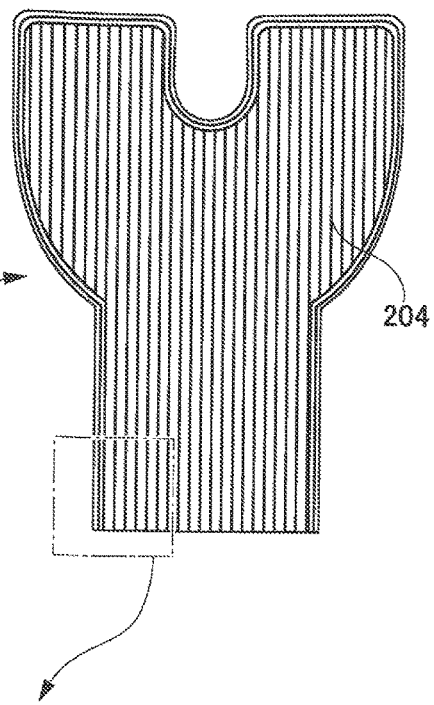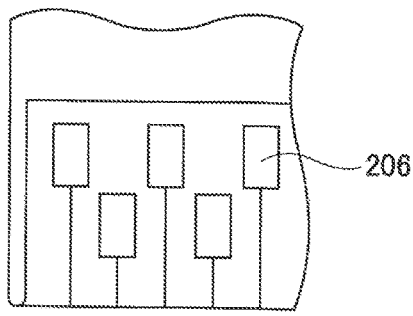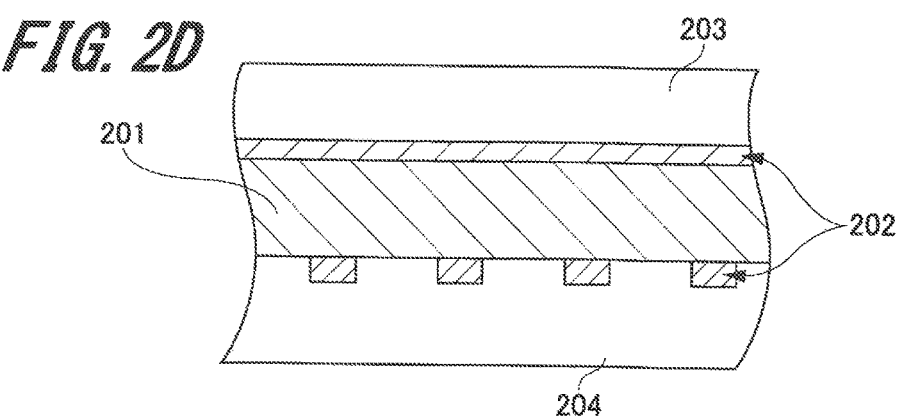

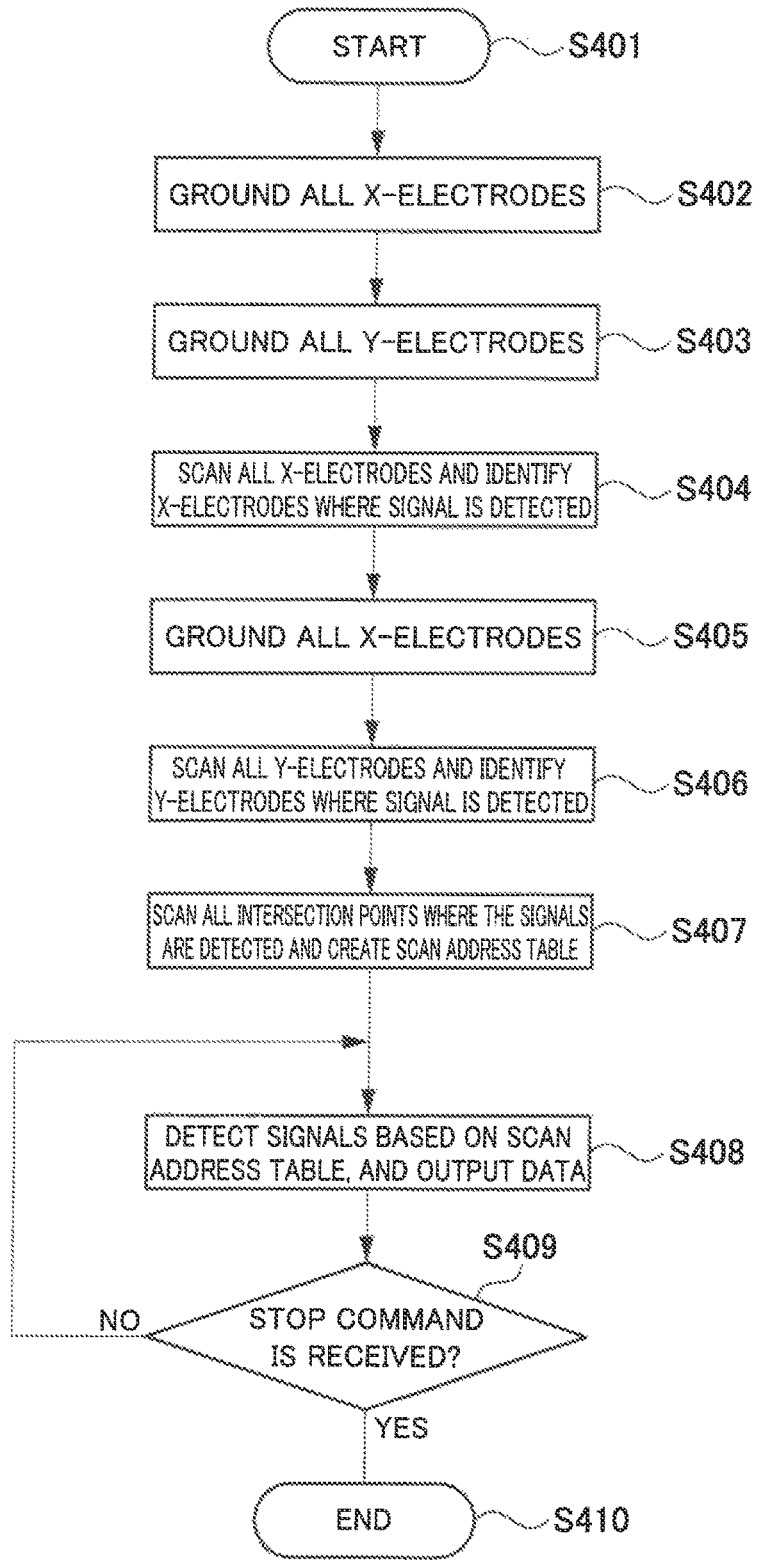

FIG. 5A
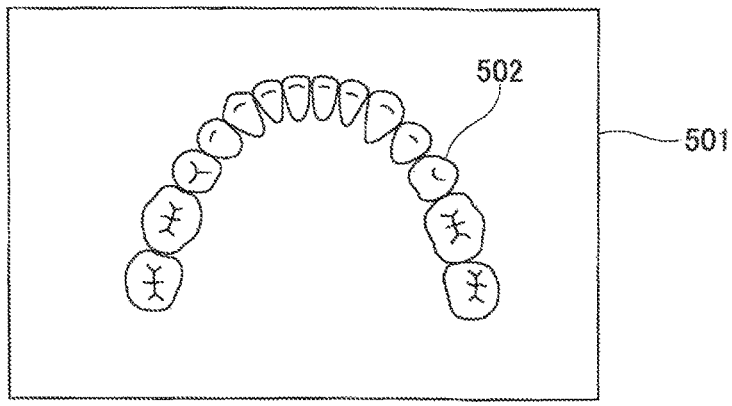
FIG. 5B
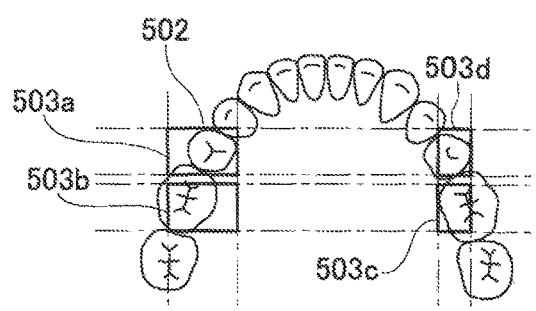
FIG. 5C
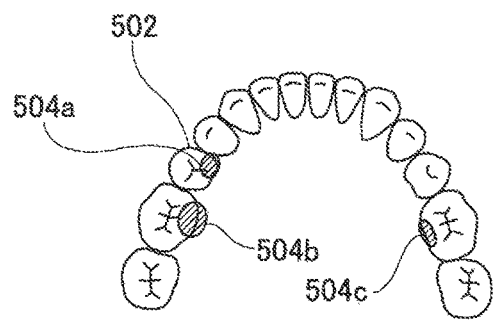
FIG. 6
| HEADER | X-COORDINATE | Y-COORDINATE | SIGN | SENSOR DETECTION VALUE | FOOTER |

OCCLUSION MEASUREMENT DEVICE AND METHOD FOR DETECTING OCCLUSAL FORCE

TECHNICAL FIELD

The present invention relates to an occlusion measurement device and an occlusal force detecting method for a dentist, a dental technician or the like to acquire information about occlusion of a patient.

BACKGROUND ART

Health maintenance is essential for people to improve their QOL (quality of life). In the medical field, various types of innovation in medical practices are carried out to support health maintenance. In recent years, improvement in performance of electronic devices also contributes to the innovation in medical practices. However, there still are some medical practices in which no improvement has been made yet. The present invention relates to acquiring information about occlusion of a patient and performing occlusion analysis, which is one of those medical practices in which improvement is being eagerly anticipated.

At present, an occlusion visual-check method using a red carbon sheet is adopted by almost all dental technicians or the like to perform occlusion analysis for a patient. When the patient bites the red carbon sheet, the red carbon will be adhered to the teeth of the patient. The carbon adhered to the teeth indicates a fact that upper teeth and lower teeth contact with each other by occlusion.

Patent Literature 1 is a document describing a prior art relating to a contact detector for measuring occlusion, in which a resistance film is used.

Patent Literature 2 is a document describing an art relating to a method for quickly detecting pressure distribution of a tactile matrix sensor.

CITATION LIST

Patent Literature

PTL 1: Japanese Examined Patent Publication No. H07-20478
PTL 2: Japanese Unexamined Patent Application Publication No. H07-190870

SUMMARY OF INVENTION

Technical Problem

With the method for visually recognizing an occlusion portion using a red carbon sheet, although the areas where the teeth of the dentition occlude each other can be recognized, there exist some problems such as: (1) the order in which the teeth of the dentition occlude each other cannot be known; (2) the strength with which the teeth of the dentition occlude each other cannot be known; (3) the areas where the teeth occlude each other, as viewing the entire dentition from a higher perspective, cannot be recognized at a glance; and (4) since the amount of the transcribed red carbon changes depending on the type of the tooth, such as natural tooth, metal tooth, prosthetic tooth and the like, it is likely to be inaccurate grasp of the occlusion state. Particularly, in order to grasp the occlusion state of the entire dentition, some dental technicians have to do troublesome work such as inserting a mirror into the mouth of the patient to take a photo with a digital camera.

The problem with the occlusion measurement device, in which a sensor sheet using a resistance film is used, disclosed in Patent Literature 1 is that it has lower resolution, and that such device is barely used due to high priced sensor sheet.

The problem with the art disclosed in Patent Literature 2 is that although it can find one contact group on the matrix sensor, it cannot be applied to a case where there exist a plurality of contact groups on the matrix surface.

To solve the aforesaid problems, an object of the present invention is to provide an occlusion measurement device, as well as an occlusal force detecting method, capable of outputting various types of information about occlusion analysis quickly and accurately.

Solution to Problem

To solve the aforesaid problems, an occlusion measurement device according to an aspect of the present invention comprises a sensor sheet, an occlusal force detecting device, and an information processing device.

The sensor sheet includes a pressure-sensitive film, a plurality of X-electrodes formed on one surface of the pressure-sensitive film, and a plurality of Y-electrodes perpendicular to the plurality of X-electrodes and formed on the other surface of the pressure-sensitive film.

The occlusal force detecting device includes: a differential amplifier that outputs a relative potential between one of the plurality of X-electrodes and one of the plurality of Y-electrodes; an A/D converter that outputs data based on the output signal of the differential amplifier; a first multiplexer connected between the plurality of X-electrodes and the differential amplifier; a second multiplexer connected between the plurality of Y-electrodes and the differential amplifier; and a controller that controls the first multiplexer and the second multiplexer, generates address information of the X-electrodes and Y-electrodes, and outputs the generated address information and the aforesaid data to a subsequent device. The controller controls the first multiplexer and second multiplexer to connect either one electrode group of the plurality of X-electrodes and plurality of Y-electrodes to a node with a constant voltage, while detecting the potential of each electrode of the other electrode group of the plurality of X-electrodes and plurality of Y-electrodes, then, after identifying a specific address range defined by electrodes where a predetermined potential has been detected, scans intersection points between an electrode group where the predetermined potential is detected among the plurality of X-electrodes and an electrode group where the predetermined potential is detected among the plurality of Y-electrodes to identify a scan address area defined by intersection points where predetermined relative potentials are to be detected, and outputs the relative potentials between the X-electrodes and the Y-electrodes of the intersection points included in the scan address area from the differential amplifier.

The information processing device includes: an integration operation processing section that performs integration operation processing on data which indicates address information of places where pressure based on an occlusal force is applied to a dentition and which indicates a change of the occlusal force, for each piece of the address information; and a moving image generation processing section that creates, on the basis of the data integrated by the integration operation processing section, moving image data based on the address information.

Further, to solve the aforesaid problems, a method for detecting occlusal force according to another aspect of the present invention comprises a specific address range identifying step, a scan address area identifying step, a relative potential detecting step, and an integration operation processing step.

The specific address range identifying step is adapted to connect either one electrode group of a plurality of X-electrodes and a plurality of Y-electrodes of a sensor sheet to a node with a constant voltage, while detecting the potential of each electrode of the other electrode group of the plurality of X-electrodes and plurality of Y-electrodes to identify a specific address range defined by electrodes where a predetermined potential has been detected, wherein the sensor sheet includes a pressure-sensitive film, the plurality of X-electrodes formed on one surface of the pressure-sensitive film, and the plurality of Y-electrodes perpendicular to the plurality of X-electrodes and formed on the other surface of the pressure-sensitive film.

The scan address area identifying step is adapted to scan intersection points between an electrode group where the predetermined potential is detected among the plurality of X-electrodes identified in the specific address range identifying step and an electrode group where the predetermined potential is detected among the plurality of Y-electrodes to identify a scan address area defined by intersection points where predetermined relative potentials are to be detected.

The relative potential detecting step is adapted to detect the relative potentials between the X-electrodes and the Y-electrodes of the intersection points included in the scan address area.

The integration operation processing step is adapted to perform integration operation processing on the relative potentials obtained in the relative potential detecting step.

Advantageous Effects of Invention

With the present invention, it is possible to provide an occlusion measurement device, as well as an occlusal force detecting method, capable of outputting various types of information about occlusion analysis quickly and accurately.

Problems, configurations and effects other than the above will become clear by describing below embodiment.

BRIEF DESCRIPTION OF DRAWINGS

FIG. 2A, FIG. 2B, FIG. 2C and FIG. 2D are views explaining the configuration of a sensor sheet;

FIG. 4 is a flowchart showing a flow of the operation of the signal processing device;

FIG. 5A, FIG. 5B and FIG. 5C are schematic views explaining the flow of an operation for a controller to identify a scanning range of the sensor sheet;

FIG. 6 shows an example of the format of a data frame outputted from the signal processing device to an information processing device;

DESCRIPTION OF EMBODIMENTS

[Entire Configuration of Occlusion Measurement Device]

Figure 1:
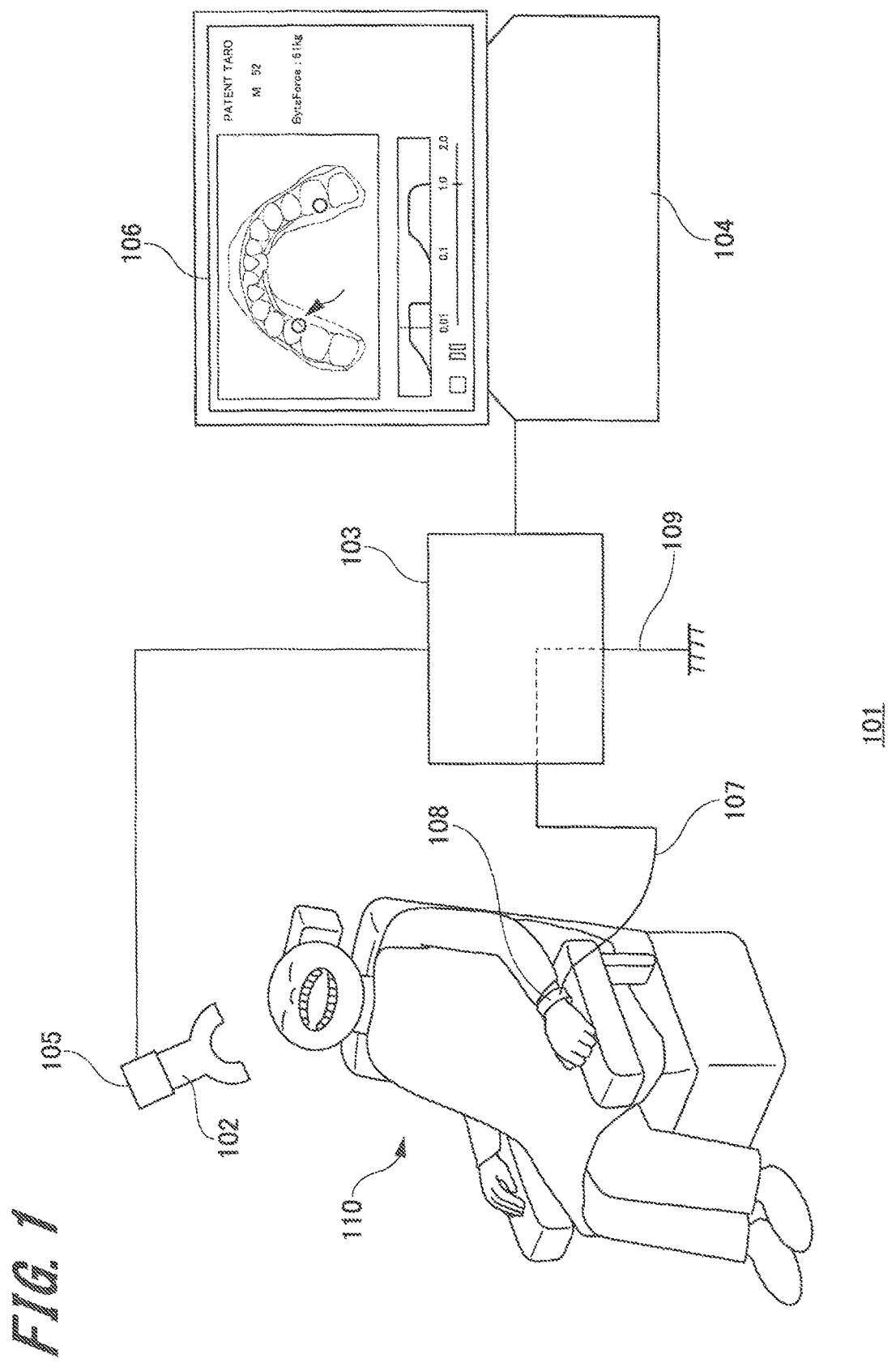
FIG. 1 is a block diagram showing the entire configuration of an occlusion measurement device according to an embodiment of the present invention.

FIG. 1 is a block diagram showing the entire configuration of an occlusion measurement device 101 according to an embodiment of the present invention.

The occlusion measurement device 101 includes a sensor sheet 102, a signal processing device 103, and an information processing device 104.

The sensor sheet 102 is used to perform occlusion analysis for a patient 110, and therefore is formed in a U-shape so as to cover the dentition of the patient 110. The sensor sheet 102 is connected to the signal processing device 103 through a dedicated connector 105.

The signal processing device 103 converts an analog voltage signal outputted from the sensor sheet 102 into digital data, and sends the digital data to the information processing device 104.

The information processing device 104 is formed by a known personal computer, and is adapted to generate, based on the digital data received from the signal processing device 103, moving image data for performing occlusion analysis, and displays a moving image on a display 106.

The sensor sheet 102 is combined with the signal processing device 103 to form an occlusal force detecting device.

In order to reduce hum noise (which is caused by electric lamp lines) and/or the like included in the output signal of the sensor sheet 102, the signal processing device 103 has one end of a patient grounding wire 107 connected thereto. The other end of the patient grounding wire 107 is connected to a wristband 108 wrapped around a wrist of the patient 110. In order to reduce hum noise (which is caused by electric lamp lines) and/or the like, the signal processing device 103 itself also has one end of a device grounding wire 109 connected thereto. The other end of the device grounding wire 109 is grounded. The patient grounding wire 107 and device grounding wire 109 cause the potential of a grounding node of a circuit within the signal processing device 103, the potential of the body of the patient 110 and the potential of the earth-surface to be equal to each other, so that hum noise or the like mixed into the signal outputted from the sensor sheet 102 is reduced.

[Configuration of Sensor Sheet 102]

The sensor sheet 102 of the present embodiment is a capacitive sensor which uses an organic piezoelectric film 201.

FIG. 2A, FIG. 2B, FIG. 2C and FIG. 2D are views for explaining the configuration of the sensor sheet 102.

FIG. 2A is an external view showing a front side of the sensor sheet 102. The sensor sheet 102 is formed substantially in a horseshoe shape so as to largely cover the dentition of the patient 110. A plurality of electrode wires 202 are printed on the front side of the sensor sheet 102, the electrode wires 202 extending in the transverse direction of the sensor sheet 102.

FIG. 2B is an external view showing a rear side of the sensor sheet 102. A plurality of electrode wires 202 are printed on the rear side of the sensor sheet 102, the electrode wires 202 extending in the longitudinal direction of the sensor sheet 102.

FIG. 2C is a partially enlarged view of a terminal portion of the sensor sheet 102. FIG. 2D is an enlarged view of a cross-section of the sensor sheet 102.

The sensor sheet 102 has an organic piezoelectric film 201 provided at its center, wherein the organic piezoelectric film 201 is formed of polyamino acid, PVDF (PolyVinylidene DiFluoride) and the like. The front face and rear face of the organic piezoelectric film 201 each have an electrode sheet bonded thereto, wherein the electrode sheet has a plurality of electrode wires 202 printed thereon. Hereinafter, the electrode sheet bonded to the front face is referred to as a "Y-electrode sheet 203", and the electrode sheet bonded to the rear face is referred to as an "X-electrode sheet 204". The electrode wires 202 formed on the X-electrode sheet 204 and the electrode wires 202 formed on the Y-electrode sheet 203 are perpendicular to each other at 90 degrees.

The X-electrode sheet 204 is formed by printing the electrode wires 202, with an organic conductive ink or the like, on an electrical insulating thin film (a first protective film) formed of polyethylene terephthalate resin (PET resin) or the like. Similarly, the Y-electrode sheet 203 is also formed by printing the electrode wires 202 on a thin film (a second protective film). The X-electrode sheet 204 and the Y-electrode sheet 203 each have its face printed with electrode wires 202 connected to the organic piezoelectric film 201. The thin films are provided for preventing the electrode wires 202 from being contacted with the saliva of the patient 110.

In order to achieve connection between the electrode wires 202 (which are formed by performing printing with organic conductive ink, or by performing a metal thin-film forming method, or the like) and the connector 105 at lower cost, the X-electrode sheet 204 and the Y-electrode sheet 203 in the terminal portion of the sensor sheet 102 are folded back as shown in FIG. 2C. The folded-back portion of the X-electrode sheet 204 and the Y-electrode sheet 203 is formed with lands 206 to contact with electrodes of the connector 105.

When the patient 110 bites the sensor sheet 102 having the aforesaid configuration, a pressure caused by occlusion is applied from the teeth to a portion of the organic piezoelectric film 201, so that a voltage accompanying the pressure is generated in such portion. Therefore, it becomes possible to perform occlusion analysis by performing data processing (which is to be described later) on such voltage.

Further, since the sensor sheet 102 uses the organic piezoelectric film 201, signal is detected by detecting the voltage. Unlike an inductive sensor, such as a coil or the like, it is unnecessary to reduce as much as possible the resistance value of the electrode wires 202 and/or wiring provided on the X-electrode sheet 204 and Y-electrode sheet 203. The signal outputted from the sensor sheet 102 may be amplified using a preamplifier with high impedance.

[Configuration of Signal Processing Device 103]

Figure 3A:
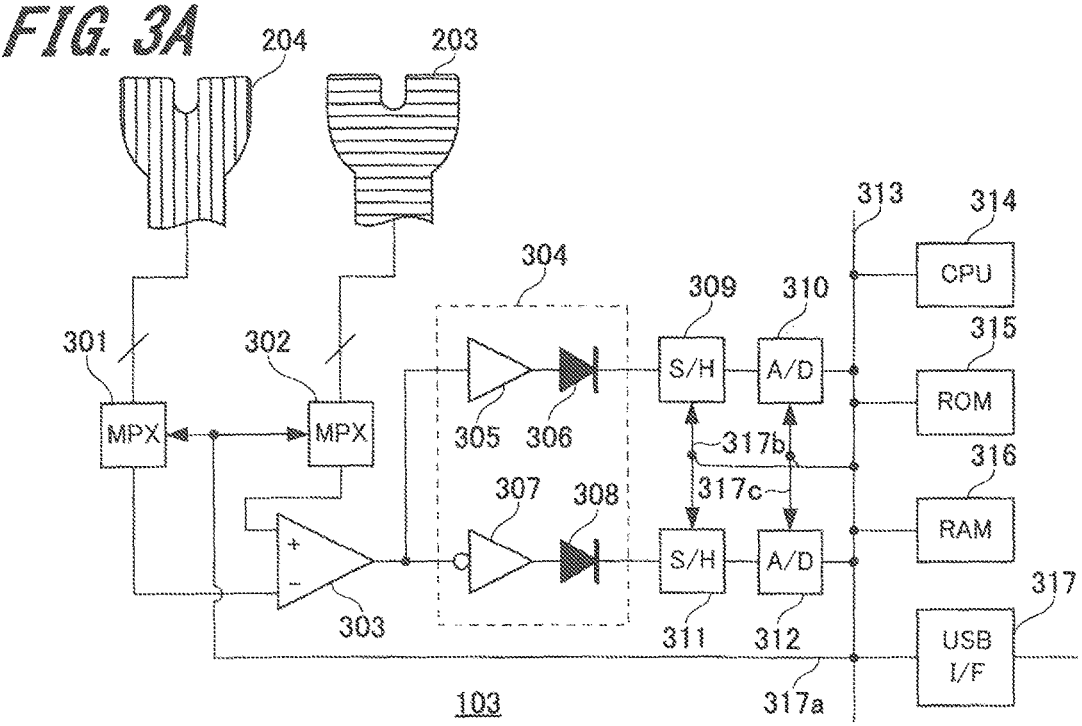
FIG. 3A and FIG. 3B are block diagrams showing hardware functions and software functions of a signal processing device.

FIG. 3A is a block diagram showing the hardware configuration of the signal processing device 103.

The X-electrode sheet 204 is connected to a first multiplexer 301, which is an analog switch adapted to selectively connect the plurality of electrode wires 202 to a subsequent circuit. Similarly, the Y-electrode sheet 203 is connected to a second multiplexer 302. Due to limited space of the drawings, the first multiplexer 301 and second multiplexer 302 are each referred to as a "MPX" in FIG. 3A and FIG. 3B.

The output signals of the first multiplexer 301 and second multiplexer 302 are inputted to a differential amplifier 303. The differential amplifier 303 outputs a relative potential between the electrode wires 202 of the X-electrode sheet 204 selected by the first multiplexer 301 and the electrode wires 202 of the Y-electrode sheet 203 selected by the first multiplexer 302.

Incidentally, in addition to the function of selectively connecting the plurality of electrode wires 202 to an output terminal, the first multiplexer 301 and second multiplexer 302 also have a function of virtually equalizing the potentials of the plurality of electrode wires 202 or grounding the plurality of electrode wires 202. The function of potential equalization or grounding will be discussed later in more detail with reference to FIG. 4.

The output signal of the differential amplifier 303 is inputted to a noise removing section 304. The noise removing section 304 includes a non-inverting amplifier 305 formed by an operational amplifier, a first operational amplifier (hereinafter referred to as a "first ideal diode 306") connected to the non-inverting amplifier 305 and functioning as an ideal diode, an inverting amplifier 307 formed by an operational amplifier, and a second operational amplifier (hereinafter referred to as a "second ideal diode 308") connected to the inverting amplifier 307 and functioning as an ideal diode.

The first ideal diode 306 only outputs the positive voltage component of the signal amplified by the non-inverting amplifier 305.

The second ideal diode 308 only outputs the positive voltage component of the signal amplified by the inverting amplifier 307.

The voltage of the output signal of the first ideal diode 306 is held by a first sample-and-hold circuit 309 for each sampling clock, and then converted into digital data by a first A/D converter 310.

Similarly, the voltage of the output signal of the second ideal diode 308 is held by a second sample-and-hold circuit 311 for each sampling clock, and then converted into digital data by a second A/D converter 312. Due to limited space of the drawings, in FIG. 3A and FIG. 3B, the first sample-and-hold circuit 309 and second sample-and-hold circuit 311 are each referred to as a "S/H", and the first A/D converter 310 and second A/D converter 312 are each referred to as a "A/D".

In other words, in an AC signal outputted from the differential amplifier 303, the positive signal component is digitalized by the first A/D converter 310, and the negative signal component is digitalized by the second A/D converter 312.

The output data of the first A/D converter 310 and the output data of the second A/D converter 312 are supplied to a bus 313. The bus 313 has a CPU 314, a ROM 315, a RAM 316, and a USB interface 317 (referred to as "USB I/F" in FIG. 3A and FIG. 3B) connected thereto, wherein the USB interface 317 is adapted to be connected to the information processing device 104.

The CPU 314, the ROM 315, the RAM 316, and the bus 313 (to which the CPU 314, the ROM 315, and the RAM 316 are connected) constitute a widely-known microcomputer.

Further, a control line 317a, a control line 317b and a control line 317c are connected to the bus 313, wherein the control line 317a is adapted to control the first multiplexer 301 and second multiplexer 302, the control line 317b is adapted to control the first sample-and-hold circuit 309 and second sample-and-hold circuit 311, and the control line 317c is adapted to control the first A/D converter 310 and second A/D converter 312. The control line 317c supplies sampling clocks having a constant period to the first A/D converter 310 and second A/D converter 312. Incidentally, in the present embodiment, the output signal of the first ideal diode 306 and the output signal of the second ideal diode 308 are each provided with one sample-and-hold circuit and one A/D converter; however, it is also possible to share one sample-and-hold circuit and one A/D converter by providing an adder to the outputs of the first ideal diode 306 and second ideal diode 308. In such case, it is necessary to provide a comparator to the outputs of the first ideal diode 306 and second ideal diode 308, and detect the sign of the outputs.

Figure 3B:
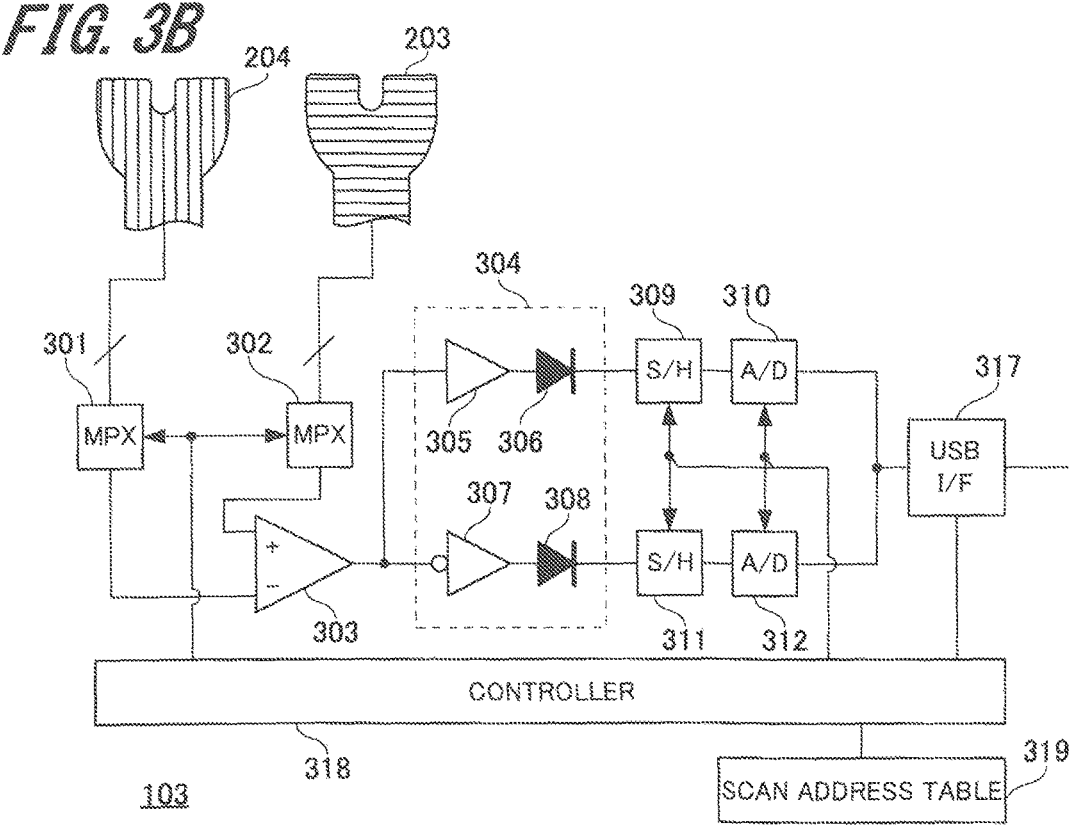

FIG. 3B is a block diagram showing software functions of the signal processing device 103.

It is known by comparing FIG. 3B with FIG. 3A that the signal processing device 103 is a microcomputer having a signal processing circuit. The software functions of the microcomputer constitute a controller 318 that controls: timing control of the multiplexers, the sample-and-hold circuits and the A/D converters; address processing (which is to be described later); and input/output of data from/to the information processing device 104 through the USB interface 317. In the process of measuring occlusal force, the controller 318 creates a scan address table 319 in the RAM 316. The details of the scan address table 319 will be described later with reference to FIG. 4, FIG. 5A, FIG. 5B and FIG. 5C.

[Operation of Signal Processing Device 103]

The signal processing device 103 performs A/D conversion, as truly as possible, on the signal outputted from the sensor sheet 102 while removing noise, and outputs the data to the information processing device 104. To detect occlusal force with the two-dimensional sensor sheet 102, the signal processing device 103 needs to continuously select a number of electrode wires 202 existing in a X-axis direction and a number of electrode wires 202 existing in a Y-axis direction respectively, and measure relative potentials of the electrode wires 202. Such operation is similar to the operation of scanning the sensor face of a touch panel or the like.

If the electrode wires 202 are densely arranged on the X-electrode sheet 204 and Y-electrode sheet 203, resolution can be improved while time required for scanning the entire sensor sheet 102 will be increased. However, unlike the touch panel or the like, the sensor sheet 102 according to the present embodiment is adapted to detect the occlusal force and the positions where the occlusal force is generated. Further, unlike the touch panel in which the object to be detected is a finger, in the present embodiment, the object to be detected is a dentition which does not largely move in directions on a detection surface. Also, it is known that, even for a healthy person, the number of bite places is less than thirty. Thus, it is possible to remarkably reduce the time required for scan by previously limiting the scanning range to positions near the bite places.

FIG. 4 is a flowchart showing the flow of the operation of the signal processing device 103. Hereinafter, the plurality of electrode wires 202 printed on the X-electrode sheet 204 will be referred to as "X-electrodes", and the plurality of electrode wires 202 printed on the Y-electrode sheet 203 will be referred to as "Y-electrodes".

When process is initiated (S401), first, the controller 318 controls the first multiplexer 301 to ground all X-electrodes (S402). Then the controller 318 controls the second multiplexer 302 to ground all Y-electrodes (S403). At this time, electric charges accumulated on all X-electrodes and Y-electrodes are discharged.

Next, the controller 318 controls the first multiplexer 301 again to only unground the X-electrodes, and then sequentially select all X-electrodes (i.e., scan all X-electrodes). Further, the controller 318 identifies the X-electrodes whose voltage is detected to be equal to or higher than a predetermined value, and stores the addresses of the identified X-electrodes in the RAM 316 (S404).

Thereafter, the controller 318 controls the first multiplexer 301 to ground all entire X-electrodes (S405). Next, the controller 318 controls the second multiplexer 302 to sequentially select all Y-electrodes to identify the Y-electrodes whose voltage is detected to be equal to or higher than a predetermined value, and store the addresses of the identified Y-electrodes in the RAM 316 (S406).

Here, description is once made for the operation of the controller 318 between step S403 to step S407, with reference to FIG. 5A, FIG. 5B and FIG. 5C.

FIG. 5A, FIG. 5B and FIG. 5C are schematic views explaining the flow of an operation for the controller 318 to identify a scanning range of the sensor sheet 102.

FIG. 5A is a schematic view showing entire address range 501 of the sensor sheet 102 grasped by the controller 318. In FIG. 5A, the address range of the sensor sheet 102 grasped by the controller 318 is in a rectangular shape that largely surrounds a dentition 502. Actually, the entire address range 501 also includes addresses where the X-electrodes and Y-electrodes do not exist. As having been described above with reference to FIG. 2A, FIG. 2B and FIG. 2C, the sensor sheet 102 is formed substantially in a horseshoe shape so as to largely cover the dentition 502. The rectangular range covering the substantially horseshoe shape is the entire address range 501. It will take long time to perform scanning if intersection points between the X-electrodes and Y-electrodes existing in the entire address range 501 are sequentially scanned one by one. In order to reduce scan time, it is necessary to employ large-scale circuits and high-performance electronic devices, and that will increase the cost.

To solve this problem, a dental technician or the like performs occlusion on a patient 110 by putting the sensor sheet 102 into the mouth of the patient 110 and asking the patient 110 to repeatedly tap the sensor sheet 102 with his (or her) teeth (typically, the dental technician asks the patient "please tap, tap, tap, tap, tap . . . ", for example). When the patient 110 taps the sensor sheet 102, due to the first occlusion, voltages are generated in the X-electrodes and Y-electrodes existing at the places where the dentition 502 contacts the sensor sheet 102. The operation of identifying the X-electrodes where the voltages are generated is performed in steps S403 and S404, and the operation of identifying the Y-electrodes where the voltages are generated is performed in steps S405 and S406.

FIG. 5B is a schematic view showing specific address ranges 503a, 503b, 503c and 503d defined by the X-electrodes and Y-electrodes where signals are detected, grasped by the controller 318 at the time of Step S406. In FIG. 5B, specific address ranges 503a, 503b, 503c and 503d grasped by the controller 318 at the time of Step S406 are each in a rectangular shape that covers places where upper teeth and lower teeth contact each other in the dentition 502.

At the time of Step S406, the controller 318 has grasped the addresses of the X-electrodes and Y-electrodes where signals had been detected. However, the area identified with the addresses of the X-electrodes and Y-electrodes where signals had been detected is nothing but the rectangular shape which includes the dentition 502 (i.e., the specific address ranges 503a, 503b, 503c and 503d), and as can be known from FIG. 5B, the specific address ranges 503a, 503b, 503c and 503d include a lot of areas where the upper teeth and lower teeth do not contact each other. For example, the specific address range 503d is an area where the upper teeth and lower teeth do not contact each other; however, since the specific address ranges 503a and 503c include places where the upper teeth and lower teeth contact each other, the specific address range 503d belongs to the specific address range formed by the controller 318.

To solve this problem, the intersection points between the X-electrodes and Y-electrodes included in the specific address ranges 503a, 503b, 503c and 503d are sequentially scanned to identify the addresses of the intersection points where the signals are detected. Further, the identified addresses are stored in the RAM 316 to create a scan address table 319 (step S407 in FIG. 4). At this time, considering the possibility that, when the patient 110 bites the sensor sheet 102 for a plurality of times, the relative position between the sensor sheet 102 and the dentition 502 may be displaced, several margins are included on left/right/up/down sides of each intersection point where the signal is detected, with the intersection point as the center.

FIG. 5C is a schematic view showing scan address areas 504a, 504b and 504c created by the controller 318 at the time of Step S407. The scan address areas 504a, 504b and 504c are formed to cover the places of the dentition 502 where the teeth contact the sensor sheet 102 when the patient bites the sensor sheet 102. In other words, the scan address areas 504a, 504b and 504c are the "positions near the bite places" mentioned above. The addresses of the intersection points between the X-electrodes and Y-electrodes included in the scan address areas 504a, 504b and 504c are elements of the scan address table 319. At the time of step S407, the intersection points included in the specific address range 503d are excluded from the scan address areas.

The explanation of the flowchart will be continued again with reference to FIG. 4.

In the steps between Steps S403 and S407, the controller 318 creates the scan address table 319 in response to each bite on the sensor sheet 102 performed by the patient 110. Thereafter, the controller 318 only scans the addresses included in the scan address table 319 to detect the relative potential of the X-electrodes and the Y-electrodes, and outputs the data (S408). Such operation is repeatedly performed until a stop command is received from the information processing device 104 which is a higher-level device ("NO" in step S409); if the stop command is received ("YES" in step S409), the controller 318 terminates the sequence of processing (S410). Incidentally, as a modification of the aforesaid operations, the present invention also includes a configuration which includes a commercially available multiplexer and which collectively separates the electrodes into several group, without performing potential equalization, to perform similar scan repeatedly.

As can be known from the above description, when the patient 110 bites the sensor sheet 102, the signal processing device 103 of the present embodiment creates the scan address table 319 based on the first occlusion, detects the second and later occlusions, and outputs data originated with occlusal force.

FIG. 6 shows an example of the format of a data frame outputted from the signal processing device 103 to the information processing device 104.

The data frame starts with "header", followed by "X-coordinate", "Y-coordinate", "sign", "sensor detection value", and "footer". It is preferred that all these fields each have a fixed bit length. Otherwise, field separators for separating neighboring fields will be necessary.

The "header" and "footer" are separators for identifying data frames between each other. If the format of the data frame is binary, the "header" and "footer" will be identified bit patterns; if the format of the data frame is text, the "header" and "footer" will be linefeed codes.

The "X-coordinate" and "Y-coordinate" each represents address information.

The "sign" represents information which shows whether the sign of the subsequent sensor detection value is positive or negative. The "sensor detection value" represents data outputted from the first A/D converter 310 or from the second A/D converter 312. When "sign" is information which indicates positive, the sensor detection value represents the value of the first A/D converter 310; and when "sign" is information which indicates negative, the sensor detection value represents the value of the second A/D converter 312.

The format of the data frame may either be binary or text; however, it is preferred that the format of the data frame is binary so as to reduce information redundancy.

[Configuration of Information Processing Device 104]

Figure 7A:
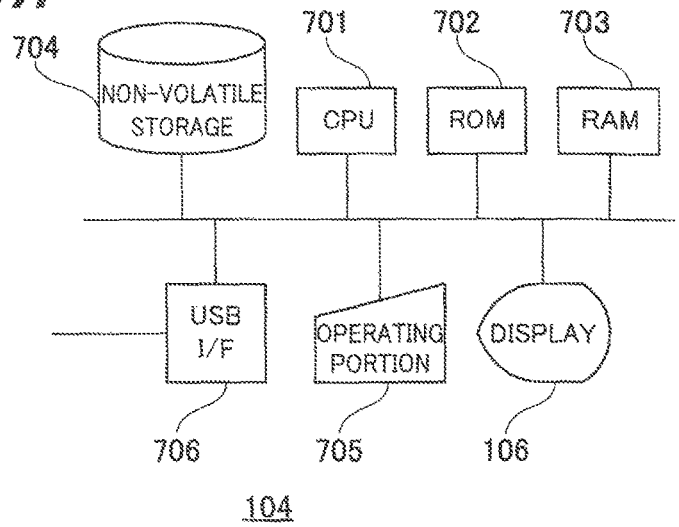
FIG. 7A and FIG. 7B are block diagrams showing hardware functions and software functions of the information processing device.

FIG. 7A is a block diagram showing the hardware configuration of the information processing device 104. The information processing device 104, which is a general personal computer, includes a CPU 701, a ROM 702, a RAM 703, a non-volatile storage 704 (such as a hard disc device or the like), an operating portion 705 (such as a keyboard or the like), the display 106, and a USB Interface 706 which is connected to the signal processing device 103; all these components are connected to the bus 313. The non-volatile storage 704 has a program stored therein, wherein the program is adapted to make a personal computer to operate as the information processing device 104 of the present embodiment.

Figure 7B:
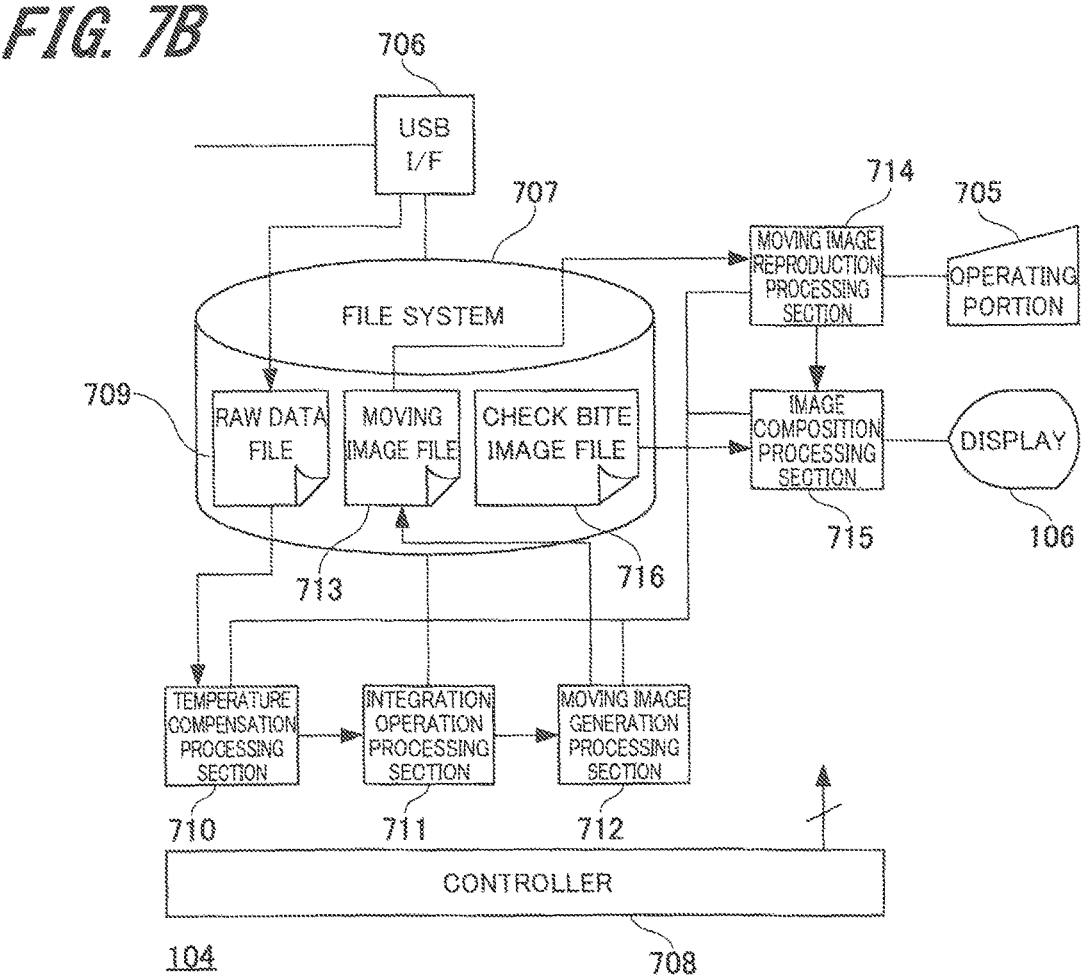

FIG. 7B is a block diagram showing software functions of the information processing device 104.

The data outputted from the signal processing device 103 is supplied to a file system 707 through the USB Interface 706, wherein the file system 707 is formed in the non-volatile storage 704. Under the control of a controller 708, the file system 707 adds time information to the data received from the signal processing device 103, and once stores the data in a raw data file 709.

After the raw data file 709 has been created, the controller 708 starts a temperature compensation processing section 710. The temperature compensation processing section 710 reads the raw data file 709 to perform temperature compensation arithmetic processing.

After the temperature compensation processing section 710 has completed the temperature compensation arithmetic processing of the raw data file 709, the controller 708 starts an integration operation processing section 711. The integration operation processing section 711 reads the data having been subjected to the temperature compensation arithmetic processing to perform integration operation processing.

After the integration operation processing section 711 has completed the integration operation processing of the data, the controller 708 starts a moving image generation processing section 712. The moving image generation processing section 712 reads the data having been subjected to integration operation processing and the address information (the X-coordinate and Y-coordinate) included in the raw data file 709, expands the read data into a bit map, and further, codes different areas of the bit map with different colors according to the strength of the occlusal force (or superimposes a bar graph on the bit map according to the strength of the occlusal force) to create a moving image file 713 in the file system 707. By performing color-coding processing corresponding to the occlusal force, the moving image generation processing section 712 creates a moving image in which change in occlusal force with time is indicated as change in color, similar to a widely-known thermography.

After the moving image file 713 has been created, it is possible for the information processing device 104 to play the moving image on the display 106. Following the operation of the operating portion 705, a moving image play processing section 714 decodes the moving image file 713 to play moving image.

An image composition processing section 715 superimposes the moving image data outputted from the moving image play processing section 714 onto a check bite image file 716 previously stored in the file system 707, and displays the image on the display 106. The term "check bite" means an operation of letting the patient 110 to bite a warmed silicon impression material so as to form a tooth mold in the silicon impression material; and a check bite image means an image of such tooth form.

There is a possibility that the signal outputted from the sensor sheet 102, which has the organic piezoelectric film 201, may include offset noise that depends on temperature. Such component depending on temperature can be removed by referring to the values of the addresses of the intersection points where pressure is not applied, among the addresses stored in the scan address table 319, and subtracting the values of the addresses of the intersection points where pressure is not applied from the values of the addresses of the intersection points where pressure is applied. The temperature compensation processing section 710 is adapted to perform the aforesaid operation.

Further, the sensor sheet 102, which has the organic piezoelectric film 201, outputs the change in pressure applied to the sensor sheet 102 as a voltage signal. In other words, the sensor sheet 102 outputs a differential signal of the pressure. Thus, in order to display the occlusal force on the display 106, an integration operation has to be performed on the data obtained from the sensor sheet 102. For such purpose, the information processing device 104 is provided with the integration operation processing section 711.

The temperature compensation processing and the integration operation processing need to be performed on all intersection points where the occlusal force is detected. The generation of the scan address table 319 (which is described with reference to FIG. 4, FIG. 5A, FIG. 5B and FIG. 5C) is also necessary for reducing such processing as much as possible.

[Regarding Integration Operation Processing]

Figure 8A:
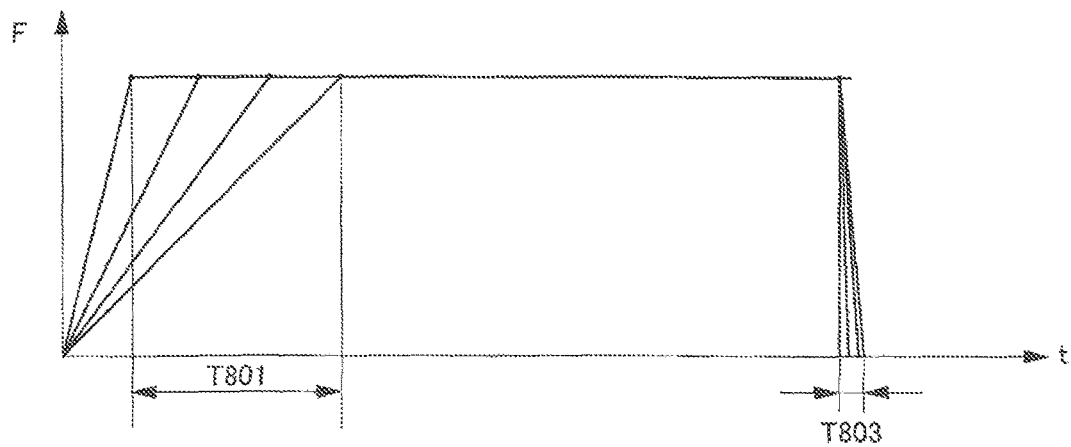
FIG. 8A and FIG. 8B are graphs schematically showing change of an occlusal force on the time axis, and change of a signal detected from the sensor sheet on the time axis.
Figure 8B:
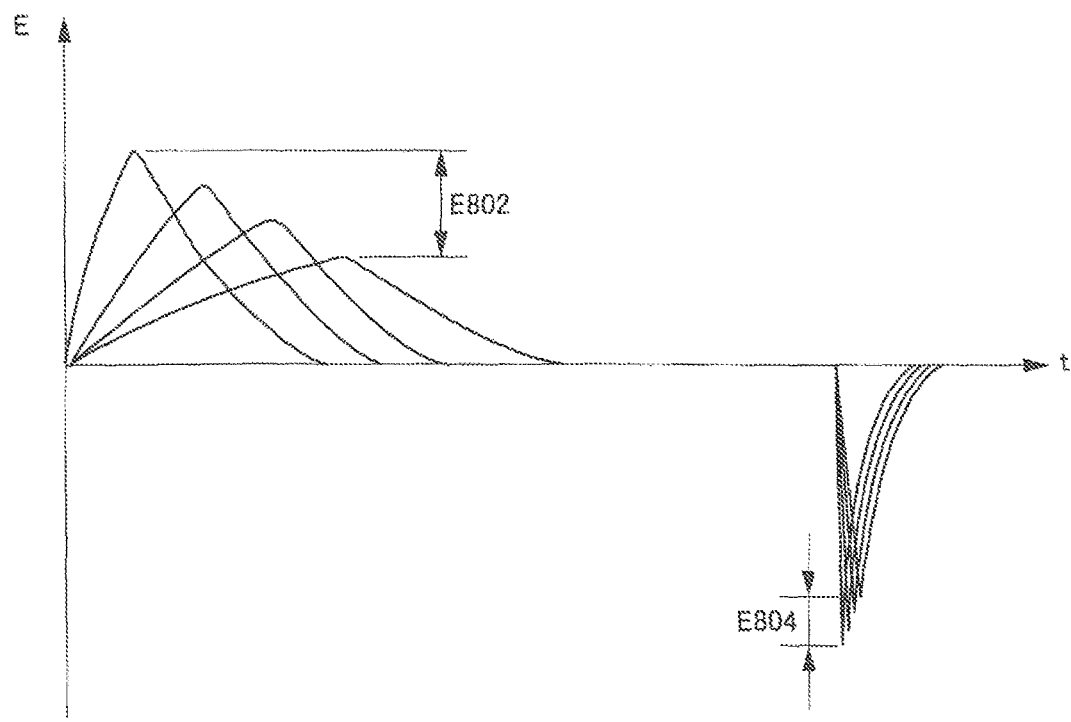

FIG. 8A is a graph schematically showing the change of the occlusal force on the time axis. FIG. 8B is a graph schematically showing the change of the signal detected from the sensor sheet 102 on the time axis. The graph of FIG. 8A and the graph of FIG. 8B coincide with each other on the time axis. FIG. 8A and FIG. 8B are graphs obtained based on a assumption that the patient 110 bites the sensor sheet 102 with a constant maximum occlusal force.

As described above, in order to calculate the occlusal force to be displayed on the display 106, an integration operation needs to be performed on the raw data obtained from the sensor sheet 102. A period from the time when the teeth of the patient 110 bite the sensor sheet 102 (i.e., applying pressure) to the time when the clenched teeth of the patient 110 are separated away from the sensor sheet 102 (i.e., reducing pressure) is defined as one cycle, and the integration operation processing of the integration operation processing section 711 is performed in unit of one cycle. One cycle is a time length ranging from about 0.2 second to several seconds unless the patient 110 has an awareness of occlusion.

When the patient 110 bites the sensor sheet 102, the occlusal force changes as shown in FIG. 8A. When the teeth are biting the sensor sheet 102, the rise of the occlusal force shows large variation on the time axis. As shown in FIG. 8B, a variation T801 appears as a voltage difference E802 of the voltage signal outputted from the sensor sheet 102. Thus, if performing integration operation based on the rise of the signal obtained from the sensor sheet 102, there will be a concern that the result may contain large error. To solve this problem, in the present invention, the bite places are scanned at a high speed for many times during the period of one cycle by previously limiting the scanning range. The occlusal force can be accurately obtained by adding A/D converted outputs of the same address obtained every time the scan is performed. For example, the change of the signal obtained from the sensor sheet 102 during the period of one cycle can be detected with high accuracy if the sampling clocks used in the first A/D converter 310 and second A/D converter 312 are set to a constant frequency of 1 KHz or higher, more preferably 1 MHz or higher.

If the patient 110 bites the sensor sheet 102 slowly (i.e., if the rise time of the output of the sensor when applying pressure is long), integration error will become large. On the other hand, when separating clenched teeth away from the sensor sheet 102, the fall of the occlusal force shows little variation on the time axis (T803). Thus, as shown in FIG. 8B, when separating clenched teeth away from the sensor sheet 102, the voltage signal outputted from the sensor sheet 102 shows little variation in voltage (E804). In other words, integration operation processing with relatively small error can be expected by calculating the maximum value of the occlusal force from the signal component in the negative direction of the voltage signal of the sensor sheet 102. Thus, in the integration operation processing, since calculation is performed based on a value of the occlusal force at the time while the pressure is being reduced, the integration operation processing is an operation processing performed tracing back the time axis. Thus, it is necessary to once file the data outputted from the signal processing device 103 as the raw data file 709.

Incidentally, the occlusal force may also be grasped using the sensor output obtained while applying or releasing pressure. At this time, the integration operation is achieved by integrating the digital value obtained by A/D converting the signal obtained by performing scanning for a plurality of times during the period of one cycle. If the values obtained by performing integration operation have the same pressure amount applied to the sensor sheet 102, the integrated values will be substantially the same value. The greater the number of times for which the scanning is performed within one cycle, the higher the accuracy of the integration value, which is proportional to the occlusal force regardless of waveform, will be. Incidentally, the number of times for which the scanning is performed within one cycle is inversely proportional to the area of the scan address area.

[Display Screen]

Figure 9:
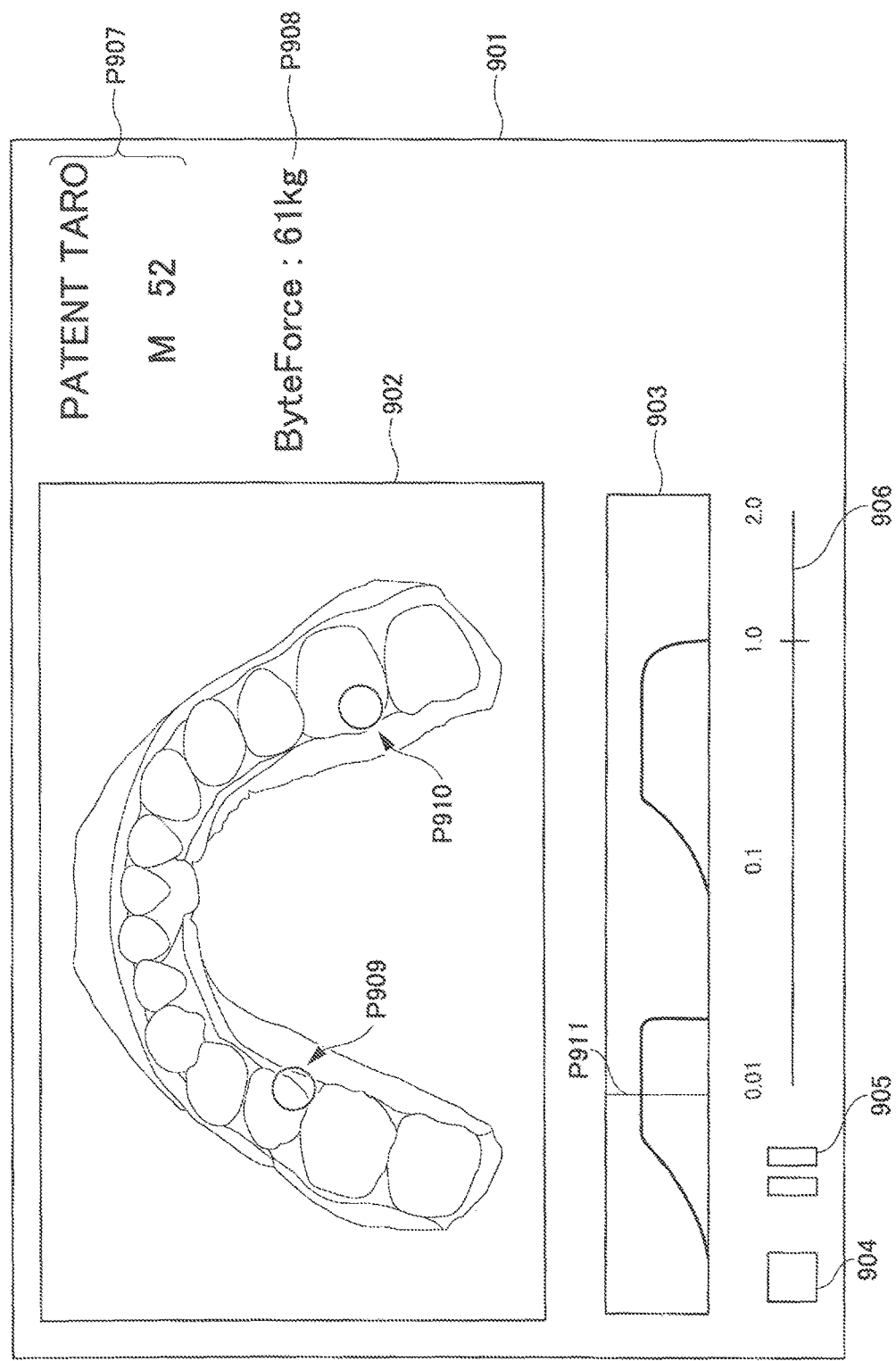
FIG. 9 shows an example of a display screen displayed on a display.

FIG. 9 shows an example of display screen displayed on the display 106.

A moving image display area 902, an occlusal force display area 903, a stop button 904, a play/pause button 905, a play speed indicating scale 906 are displayed on a screen 901. Further, patient information P907 (such as name of the patient 110) and maximum occlusal force information P908 are displayed in a portion of the screen 901. A play pointer P911 is displayed in the occlusal force display area 903, and play position can be changed by moving the play pointer P911 with a pointing device such as a mouse (not shown).

Displayed in the occlusal force display area 903 is a check bite image in which the places where the occlusal force is generated are either color-coded or superimposed with a bar graph corresponding to the occlusal force. Further, a place P909 where occlusal force is first generated on the sensor sheet 102 when performing occlusion, and a place P 910 displayed in the occlusal force display area 903 are marked and displayed.

When creating image file based on the data outputted from the integration operation processing section 711, the moving image generation processing section 712 performs color-coding process according to the strength of the occlusal force. For example, similar to a widely-known contour map, the intersection points where the occlusal force is generated are color-coded using: "blue→green→greenish yellow→yellow→orange→red" in this order from the weak side of the occlusal force. Further, the image composition processing section 715 superimposes the moving image data outputted by the moving image play processing section 714 onto the check bite image, so that it can be known, at a glance, that where the upper teeth and the lower teeth contact each other and at what level the occlusal force is generated.

Furthermore, the moving image play processing section 714 reads and scans the moving image file 713 or the raw data file 709 to identify an intersection point where first signal change appears on the time axis. Since the identified intersection point represents the point where the sensor sheet is first touched by the teeth when performing occlusion, the moving image play processing section 714 marks such intersection point in the moving image display area 902.

Further, the dental technician or the like asks the patient 110 to strongly clench his (or her) teeth. As a result, a strong occlusal force becomes data and appears as the raw data file 709. The moving image play processing section 714 integrates the value of all intersection points where occlusal force is generated on the same time axis, and displays a value of the time indicating the maximum value, as the maximum occlusal force, on the lateral side of the moving image display area 902.

In addition to the aforesaid embodiment, the present invention also includes the following applications (a) to (d).
(a) The electrode wires 202 may also be formed by printing the electrode wires 202, with an organic conductive ink, on the organic piezoelectric film 201, instead of being limited to performing print processing on a sheet functioning as a cover, such as the method for forming the aforesaid X-electrode sheet 204 and Y-electrode sheet 203. In such a case, since a land 206 is formed on the organic piezoelectric film 201, in the organic piezoelectric film 201, only the portion where the land 206 is formed needs to be exposed, without the need to fold back the X-electrode sheet 204 and Y-electrode sheet 203 as shown in FIG. 2C.

Further, the electrode wires 202 may also be formed by forming a thin film using a sputter method, or by bonding a metal foil such as a copper foil.
(b) The present invention also includes a configuration in which the signal processing device 103 is provided with the non-volatile storage 704, and the raw data file 709 is generated by the signal processing device 103. In such a case, the signal processing device 103 may provide the information processing device 104 with a USB storage function in which the raw data file 709 is stored, without the need to establish the data frame as shown in FIG. 6 and perform communication between the signal processing device 103 and the information processing device 104.
(c) There are physical limitations to increase the density of the electrode wires 202 to improve the resolution of the sensor sheet 102. Further, increasing the density of the electrode wires 202 will increase the cost. In order to improve the resolution of the occlusal force detecting device while reducing the cost, an interpolating operation method may also be employed in which there is a virtual electrode wire 202 between adjacent electrode wires 202. Further, in order to reduce, as much as possible, area where the occlusal force cannot be measured, it is preferred that the width of the electrode wires 202 is as large as possible, and the gap between adjacent electrode wires 202 on the same plane is as small as possible.
(d) The present invention also includes a configuration in which, in the case where no check bite image has been taken from the patient 110, sample image data of a standard dentition, instead of the check bite image file 716, is superimposed onto the moving image display area 902. In the case where there is a check bite image, alignment between the check bite image and the bite places can be easily performed with a mouse by using at least two addresses on the clenched dentition.
(e) In step S402 and step S403 of FIG. 4, all X-electrodes and Y-electrodes are grounded in order to discharge electric charges accumulated on the plurality of electrode wires 202 printed on the X-electrode sheet 204 and Y-electrode sheet 203. However, the node to discharge the electric charges accumulated on the plurality of electrode wires 202 does not necessarily have ground potential. For example, in many cases where the signal processing device 103 is powered by a single power source, in order for the operational amplifier to detect the voltage signal generated from the sensor sheet 102, a potential equal to half of the voltage of the single power source (i.e., a middle point voltage) is obtained by dividing the voltage of the single power source with a resistor or the like. In such a case, the electrode wires 202 are connected to the node of the middle point voltage to discharge the electric charges. Also, in such a case, it does not matter even if the potential of the body of the patient 110 is ground potential. Further, the node to discharge the electric charges of the electrode wires 202 may be an arbitrary node fixed to a constant voltage, instead of being limited to the middle point voltage.
(f) The sensor sheet 102 of the aforesaid embodiment is a capacitive sensor which uses an organic piezoelectric material; however, a resistance film may also be used as the sensor sheet. For example, the art disclosed in Japanese Unexamined Patent Application Publication No. 2013-48680 may also be applied. In other words, any matrix sensor may be applied. In the case where a sensor sheet 102 using a resistance film is employed, since the relationship between the occlusal force and the resistance detected from the current (or voltage) signal is a linear relationship, the integration operation processing section 711 of the information processing device 104 can be omitted.

In the present embodiment, the occlusion measurement device 101, the occlusal force detecting device, and the information processing device 104 are disclosed, wherein the occlusal force detecting device is formed by the sensor sheet 102 and the signal processing device 103. The present embodiment disclosed above has the following advantageous effects (1) to (7).

(1) The both surfaces of the organic piezoelectric film 201 are provided with the X-electrode sheet 204 and Y-electrode sheet 203 each are formed with a plurality of electrode wires 202, and thereby it is possible to achieve a sensor sheet 102 for detecting occlusal force with lower cost and higher resolution compared to prior arts. Since such sensor sheet 102 can be produced at extremely low cost compared to prior arts, it can be used in a disposable, and therefore sanitary can be kept.

(2) An occlusal force detecting device capable of reliably detecting a signal originated with occlusal force can be achieved by detecting voltage with the differential amplifier 303 through the multiplexer which selects the electrode wires 202 formed on the X-electrode sheet 204 and Y-electrode sheet 203 bonded on the both surfaces of the organic piezoelectric film 201.

(3) An occlusal force detecting device capable of sophisticatedly performing measurement with minimum data amount can be achieved by letting the patient 110 to bite the sensor sheet 102 for two or more times, where the first bite is performed to identify the places where a pressure originated with occlusal force is generated on the sensor sheet 102, and the second or later bite is performed to detect the occlusal force of the occlusion.

(4) The information processing device 104 performs integration processing for each intersection point for raw data outputted from the occlusal force detecting device having the sensor sheet 102 which uses the organic piezoelectric film 201, to create occlusal force data, wherein the raw data includes address information of each intersection point and data obtained based on a signal indicating a change in occlusion force. Owing to the integration operation processing, it is possible to achieve an information processing device 104 capable of sophisticatedly performing measurement on the time axis.

(5) The information processing device 104 performs, after creating the occlusal force data, image mapping processing based on the address of each intersection point, creates moving image of occlusal force, and displays the moving image of occlusal force on the display 106. Owing to the image mapping processing, it is possible to achieve an information processing device 104 capable of grasping the places where occlusal force is generated on the entire dentition and the change of the occlusal force at a glance. Obviously a still image can be selected at this time.

(6) After creating the moving image of occlusal force, the information processing device 104 superimposes the moving image of occlusal force onto the check bite image, and displays the superimposed image. An information processing device 104 capable of grasping the places where occlusal force is generated on the entire dentition and the change of the occlusal force at a glance can be achieved by displaying the superimposed image.

(7) After creating the moving image of occlusal force, the information processing device 104 marks and displays a place where occlusal force is first generated on the sensor sheet 102. An information processing device 104 capable of grasping the most protruded place on the entire dentition at a glance can be achieved by performing mark and display.

The embodiments of the present invention have been described above. It is to be understood that the present invention is not limited to the embodiments described above, and various modifications and applications can be made without departing from the spirit and scope of the present invention.

For example, in order to explain the present invention more understandable, in the aforesaid embodiments, the structure of a device and a system are described in a concrete and detailed manner; however, the present invention is not necessarily to include all these configurations. It is possible to substitute a part of the configuration of one embodiment with the configuration of another embodiment, and further, it is also possible to add the configuration of one embodiment to the configuration of another embodiment. Further, it is also possible to add/omit/substitute other configuration to/from/with a part of each of the aforesaid embodiments.

Further, a part or all of the aforesaid each configuration, function, processing section may also be achieved by hardware, such as by being designed with an integrated circuit, for example. Further, the aforesaid each configuration, function and the like may also be achieved by software for explaining and executing a program that causes a processor to achieve the function thereof. Information about the program, table and file which achieve each function can be stored in a volatile or non-volatile storage (such as a memory, a hard disk, a SSD (solid state drive) or the like), or a recording medium (such as an IC card, an optical disk or the like).

Note that, regarding control lines and information lines, only the control lines and information lines indispensable to describe the specification are indicated, so that it does not mean all control lines and information lines of the product are indicated in the specification. Actually almost all configurations are connected with each other.

REFERENCE SIGNS LIST

101 occlusion measurement device
102 sensor sheet
103 signal processing device
104 information processing device
105 connector
106 display
107 patient grounding wire
108 wristband
109 device grounding wire
110 patient
201 organic piezoelectric film
202 electrode wires
203 Y-electrode sheet
204 X-electrode sheet
206 land
301 first multiplexer
302 second multiplexer
303 differential amplifier
304 noise removing section
305 non-inverting amplifier
306 first ideal diode
307 inverting amplifier
308 second ideal diode
309 first sample-and-hold circuit
310 first A/D converter
311 second sample-and-hold circuit
312 second A/D converter
313 bus
314 CPU
315 ROM
316 RAM
317 USB interface 318 controller
319 scan address table
501 entire address range
502 dentition
503 specific address range
504 scan address area
701 CPU
702 ROM
703 RAM
704 non-volatile storage
705 operating portion
706 USB Interface
707 file system
708 controller
709 raw data file
710 temperature compensation processing section
711 integration operation processing section
712 moving image generation processing section
713 moving image file
714 moving image play processing section
715 image composition processing section
716 check bite image file
901 screen
902 moving image display area
903 occlusal force display area
904 stop button
905 pause button
906 play speed indicating scale

The invention claimed is:

1. A method for detecting occlusal force comprising:
a specific address range identifying step of holding either one electrode group of a plurality of X-electrodes and a plurality of Y-electrodes of a sensor sheet at a ground potential, while detecting the potential of each electrode of the other electrode group of the plurality of X-electrodes and the plurality of Y-electrodes to identify specific address ranges, each specific address range being defined by electrodes where a predetermined potential has been detected, wherein the sensor sheet includes a pressure-sensitive film, the plurality of X-electrodes formed on one surface of the pressure-sensitive film, and the plurality of Y-electrodes formed on the other surface of the pressure-sensitive film and extending perpendicular to the plurality of X-electrodes;

a scan address area identifying step of sequentially scanning intersection points included in the specific address ranges, the intersection points being between an electrode group where the predetermined potential is detected among the plurality of X-electrodes identified in the specific address range identifying step and an electrode group where the predetermined potential is detected among the plurality of Y-electrodes identified in the specific address range identifying step, to identify a scan address area defined by intersection points where predetermined relative potentials are to be detected and to exclude intersection points where predetermined relative potentials are not to be detected; and a relative potential detecting step of detecting the relative potentials between the X-electrodes and the Y-electrodes of the intersection points included in the scan address area.

2. The method for detecting occlusal force according to claim 1, wherein, in the scan address area identifying step, the intersection points are margined.

* * * * *